US009399772B2

(12) United States Patent
Colbert et al.

(10) Patent No.: US 9,399,772 B2
(45) Date of Patent: Jul. 26, 2016

(54) TOMATOES THAT SOFTEN MORE SLOWLY POST-HARVEST DUE TO NON-TRANSGENIC ALTERATIONS IN AN EXPANSIN GENE

(71) Applicant: ARCADIA BIOSCIENCES, INC., Davis, CA (US)

(72) Inventors: Trenton G. Colbert, Seattle, WA (US); Susan R. Hurst, Seattle, WA (US); Ann J. Slade, Bellevue, WA (US); Dayna L. Loeffler, Seattle, WA (US)

(73) Assignee: Arcadia Biosciences, Inc., Davis, CA (US)

( * ) Notice: Subject to any disclaimer, the term of this patent is extended or adjusted under 35 U.S.C. 154(b) by 127 days.

(21) Appl. No.: 14/178,851

(22) Filed: Feb. 12, 2014

(65) Prior Publication Data

US 2014/0342081 A1    Nov. 20, 2014

Related U.S. Application Data

(62) Division of application No. 13/002,103, filed as application No. PCT/US2009/049430 on Jul. 1, 2009, now abandoned.

(60) Provisional application No. 61/077,453, filed on Jul. 1, 2008.

(51) Int. Cl.
| | |
|---|---|
| *C12N 15/05* | (2006.01) |
| *A01H 1/04* | (2006.01) |
| *A01H 5/08* | (2006.01) |
| *C12N 15/01* | (2006.01) |
| *C07K 14/415* | (2006.01) |
| *A23L 1/212* | (2006.01) |
| *C12Q 1/68* | (2006.01) |

(52) U.S. Cl.
CPC *C12N 15/01* (2013.01); *A01H 5/08* (2013.01); *A23L 1/212* (2013.01); *C07K 14/415* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | | |
|---|---|---|---|---|
| 5,994,075 | A | 11/1999 | Goodfellow | |
| 6,350,935 | B1 | 2/2002 | Bennett | |
| 2003/0236208 | A1* | 12/2003 | Kmiec et al. | 514/44 |
| 2004/0053236 | A1 | 3/2004 | McCallum | |
| 2004/0250322 | A1 | 12/2004 | McCallum et al. | 800/317.4 |

FOREIGN PATENT DOCUMENTS

WO    WO 2008/034648    3/2008

OTHER PUBLICATIONS

Brummell et al. (The Plant Cell, vol. 11, 2203-2216, Nov. 1999).*
Powell et al. J. Agric. Food Chem. 2003, 51, 7450-7455.*
International Search Report for PCT/US2009/49430, dated Oct. 13, 2009.
Written Opinion of the International Searching Authority for PCT/US2009/49430, dated Oct. 13, 2009.
Brummell, Modification of Expansin Protein Abundance in Tomato Fruit Alters Softening and Cell Wall Polymer Metabolism during Ripening, The Plant Cell 11:2203-2216, 1999.
Butrym, An Apparatus for Sampling Volatile Organics from Live Plant Material Using Short Path Thermal Description, Eastern Analytical Symposium, Somerset, NJ, Nov. 1998.
Cantwell, Report to the California Tomato Commission: Tomato Variety Trials: Postharvest Evaluations for 2001.
Chen, A Rapid DNA Minipreparation Method Suitable or AFLP and Other PCR Applications, Plant Molecular Biology Reporter 17:53-57, 1999.
Colbert, High-Throughput Screening for Induced Point Mutations, Plant Physiology 126:480-484, 2001.
Edan, Color and Firmness Classification of Fresh Market Tomatoes, Journal of Food Science 62(4): 793-796, 1997.
Errington, Changes in the Force Relaxation and Compression Responses of Tomatoes During Ripening: the Effect of Continual Testing and Polygalacluronase Activity, Postharvest Biology and Technology 11:141-147, 1997.
Henikoff, Using Substitution Probabilities to Improve Position-Specific Scoring Matrices, Computer Applications in the Biosciences 12:135-143, 1996.
Innis, PCR Protocols: A Guide to Methods and Applications, Academic Press, San Diego, 1990.
Kalamaki, Simultaneous Transgenic Suppression of LePG and LeExp1 Influences Rheological Properties of Juice and Concentrates from a Processing Tomato Variety, Journal of Agricultural and Food Chemistry 51(25):7465-7471, 2003s.
Kalamaki, Transgenic Overexpression of Expansin Influences Particle Size Distribution and Improves Viscosity of Tomato Juice and Paste, Journal of Agricultural and Food Chemistry 51(25):7456-7464, 2003b.
Lesage, Measurement of Tomato Firmness by Using a Non-Destructive Mechanical Sensor, Postharvest Biology and Technology 8:45-55, 1996.
Li, Integrated platform for detextion of DNA Sequenxe Variants Using Capillary Array Electrophoresis, Electrophoresis 23(10):1499-1511, 2002.
Malundo, Flavor Quality of Frest Tomato (*Lycopersicon esculentum* Mill.) as Affected by Sugar and Acid Levels, Postharvest Biology and Technology 5:103-110, 1995,
McCallum, Target Screening for Induced Mutations, Nature Biotechnology 18:455-457, 2000s.
McCallum, Targeting Induced Local Lesions n Genomes (TILLING) for Plant Functional Genomics, Plant Physiology 123:439-442, 2000b.

(Continued)

*Primary Examiner* — Anne Kubelik
*Assistant Examiner* — Charles Logsdon

(57) ABSTRACT

A series of independent human-induced non-transgenic mutations found in an expansin gene (LeExp1) of tomato; tomato plants having these mutations in their LeExp1 genes; and a method of creating and identifying similar and/or additional mutations in the LeExp1 gene by screening pooled and/or individual tomato plants. The tomato plants of the present invention exhibit fruit that soften more slowly post-harvest without having the inclusion of foreign nucleic acids in their genomes.

14 Claims, No Drawings

(56) References Cited

OTHER PUBLICATIONS

McGuire, Reporting of Objective Color Measurements, HortScience 27(12): 1254-1255, 1992.
NG, SIFT: Predicting Amino Acid Changes that Affect Prate Function, Nucleic Acids Research 31(13):3812-3814, 2003.
Polder, Hyperspectral Image Analysis for Measuring Ripeness of Tomatoes, Paper No. 003089, 2000 American Society of Agricultural Engineers International Meeting, Milwaukee, WI, Jul. 2000.
Rose, Expression of a Divergent Expansin Gene is Fruit-Specific and Ripening-Regulated, Proceedings of the National Academy of Sciences USA 94:5955-5860, 1997.
Stewart, A Rapid CTAB DNA Isolation Technique Useful for RAPD Fingerprinting and Other PCR Applications, Bio Techniques 14(5):748-749, 1993.
Taylor, PARSENSP: A Tool for the Analysis of Nucleotid Polymorphisms, Nucleic Acids Research 31:3808-3811, 2003.
Brown TA, Genomes, 2nd edition. Oxford: Wiley-Liss; 2002. Chapter 7, Understanding a Genome Sequence. Available at <http://www.ncbi.nlm.nih.gov/books/NBK21136/>.
Civello et al., An expansin gene expressed in ripening strawberry fruit, 121 Plant Physiology, 1273-1279 (1999).
GenBank Accession No. U82123 ([online], [retrieved Jan. 23, 2013], retrieved from the internet <http://www.ncbi.nlm.nih.gov/nuccore/U82123.1>>.
McCallum et al., Targeting Induced Local Lesions IN Genomes (TILLING) for Plant Functional Genomics, 123 Plant Physiology, 439-442 (2000).
Rose at al., Detection of Expansin Proteins and Activity during Tomato Fruit Ontogeny, 123 Plant Physiology, 1583-1592 at 1584 (2000).
Rose et al., Expression of a divergent expansin gene is fruit-specific and ripening-regulated, 94 PNAS, 5955-5960 (1997).
Sol Genomics Network, Tomato locus expansin 1 submitted May 10, 2006, available at <http://solgenomics.netllocus/516/view>.

* cited by examiner

SEQUENCE LISTING

```
<160> NUMBER OF SEQ ID NOS: 11

<210> SEQ ID NO 1
<211> LENGTH: 1070
<212> TYPE: DNA
<213> ORGANISM: Lycopersicon esculentum

<400> SEQUENCE: 1
gaacttcaat tccattaaat cttaagaatg ggtatcataa ttttcatcct tgttcttctt      60
tttgtagact catgtttcaa cattgttgaa ggaagaatcc ctggtgttta ctctggtggt     120
tcatgggaaa ctgcacatgc tacatttttac ggcggaagtg atgcttctgg aacaatgggc    180
ggtgcgtgtg gttatggaaa tttatacagc caaggatacg gagttaacac agcagcactg    240
agtactgctt tgtttaacaa tggattaagt tgtggagcct gttttgaact taaatgtaca    300
aatactccta attggaaatg gtgtcttcct ggaaacccct tccattttaat cacagctacc    360 aatttctgcc caccaaatta cgcgttgcca aatgacaatg gtggctggtg taaccctcct    420
cgccctcact ttgacctcgc tatgcctatg tttctcaaac ttgctcagta ccgcgctggc    480
attgttcctg taacttatcg caggatccca tgccgaaagc aaggaggaat cagatttacc    540
atcaatggat tccgttactt caacttagtg ttgatcacga atgtagcagg tgcagggat     600 attattaagg tttgggtaaa aggaacaaag acaaattgga ttccattgag ccgtaattgg     660
```

| | | |
|---|---|---|
| ggacaaaatt ggcaatcaaa tgcggtttta actggtcaat cactctcttt cagagttaaa | 720 | |
| gctagtgacc atcgatcttc tacctcatgg aatatggttc cttctcattg gcaatttggc | 780 | |
| caaactttca tcggaaagaa tttcaaaata taaaattagt aagggtattg ttattttttaa | 840 | |
| tttgtgggaa aactaggata tttcagagtg ttgttcacct taggaaaaga aatcgagtcc | 900 | |
| tcactgaaaa ttcagataga taattaatta aattactaaa attttcgat attttgagt | 960 | |
| gtgtatcaac attttaacct aagtatggtt aaatggagag aaaggttgaa gtggctgcaa | 1020 | |
| aatcatgcag cccgcagctg ttttttttt tttacaatat acatcacaag | 1070 | |

<210> SEQ ID NO 2
<211> LENGTH: 28
<212> TYPE: DNA
<213> ORGANISM: Artificial Sequence
<220> FEATURE:
<223> OTHER INFORMATION: Synthetic Construct

<400> SEQUENCE: 2
cctggaaacc cttccatttt aatcacag                                   28

<210> SEQ ID NO 3
<211> LENGTH: 28
<212> TYPE: DNA
<213> ORGANISM: Artificial Sequence
<220> FEATURE:
<223> OTHER INFORMATION: Synthetic Construct

<400> SEQUENCE: 3
catgattttg cagccacttc aacctttc                                   28

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4 tacatttac ggcggaagtg atgcttct                                    28

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
tgattgacca gttaaaaccg catttgat                                   28

<210> SEQ ID NO 6
<211> LENGTH: 1412
<212> TYPE: DNA
<213> ORGANISM: Lycopersicon esculentum

<400> SEQUENCE: 6

| | | |
|---|---|---|
| gaacttcaat tccattaaat cttaagaatg gtatcataa ttttcatcct tgttcttctt | 60 | |
| tttgtagact catgttcaa cattgttgaa ggaagaatcc ctggtgttta ctctggtggt | 120 | |
| tcatgggaaa ctgcacatgc tacatttac ggcggaagtg atgcttctgg aacaatgggc | 180 | |
| ggtgcgtgtg gttatggaaa tttatacagc caaggatacg gagttaacac agcagcactg | 240 | |

```
agtactgctt tgtttaacaa tggattaagt tgtggagcct gttttgaact taaatgtaca    300
aatactccta attggaaatg gtgtcttcct ggaaaccctt ccattttaat cacagctacc    360
aatttctgcc caccaaatta cgcgttgcca aatgacaatg gtggctggtg taaccctcct    420
cgccctcact ttgacctcgc tatgcctatg tttctcaaac ttgctcagta ccgcgctggc    480
attgttcctg taacttatcg caggtaataa atcaattaat taaatattgt taaaaaatga    540
caaaaattct tataatagtt ggacaatcct tctctctttg agctagcttt tagggtgtga    600
attaggtcta agatctaatt tcacgtggta tcgtctcacc cgatgctgac gttcccaaaa    660
ttaaaattgc ccacgcacca gatgctaacc actggtcgtg aggtagggta ttaaaaaatg    720
acaaaagttc acatcgatga ttaatgagat gggtagactt cttacaaggc ttgggcaatc    780
ttcctccgtt tgagctaact tttgaaaata atttcaatag taacgtgtat ttgtgaaatg    840
ttcaggatcc catgccgaaa gcaaggagga atcagattta ccatcaatgg attccgttac    900
ttcaacttag tgttgatcac gaatgtagca ggtgcagggg atattattaa ggtttgggta    960
aaaggaacaa agacaaattg gattccattg agccgtaatt ggggacaaaa ttggcaatca   1020
aatgcggttt taactggtca atcactctct ttcagagtta aagctagtga ccatcgatct   1080
tctacctcat ggaatatggt tccttctcat tggcaatttg gccaaacttt catcggaaag   1140
aatttcaaaa tataaaatta gtaagggtat tgttattttt aatttgtggg aaaactagga   1200
tatttcagag tgttgttcac cttaggaaaa gaaatcgagt cctcactgaa aattcagata   1260
gataattaat taaattacta aaattttttcg atattttga gtgtgtatca acattttaac   1320
ctaagtatgg ttaaatggag agaaaggttg aagtggctgc aaaatcatgc agcccgcagc   1380 tgttttttttt ttttttacaat atacatcaca ag                              1412

<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
tcaattccat taaatcttaa gaatgggtat ca                                 32

<210> SEQ ID NO 8
<211> LENGTH: 32
<212> TYPE: DNA
<213> ORGANISM: Artificial Sequence
<220> FEATURE:
<223> OTHER INFORMATION: Synthetic Construct

<400> SEQUENCE: 8
tttccaaaag ttagctcaaa cggaggaaga tt                                 32

<210> SEQ ID NO 9
<211> LENGTH: 28
<212> TYPE: DNA
<213> ORGANISM: Artificial Sequence
<220> FEATURE:
<223> OTHER INFORMATION: Synthetic Construct

<400> SEQUENCE: 9
cctggaaacc cttccatttt aatcacag                                      28

<210> SEQ ID NO 10
<211> LENGTH: 28
```

```
<212> TYPE: DNA
<213> ORGANISM: Artificial Sequence
<220> FEATURE:
<223> OTHER INFORMATION: Synthetic Construct

<400> SEQUENCE: 10
catgattttg cagccacttc aacctttc                                              28

<210> SEQ ID NO 11
<211> LENGTH: 261
<212> TYPE: PRT
<213> ORGANISM: Lycopersicon esculentum

<400> SEQUENCE: 11

Met Gly Ile Ile Ile Phe Ile Leu Val Leu Leu Phe Val Asp Ser Cys
 1               5                  10                  15

Phe Asn Ile Val Glu Gly Arg Ile Pro Gly Val Tyr Ser Gly Gly Ser
             20                  25                  30

Trp Glu Thr Ala His Ala Thr Phe Tyr Gly Gly Ser Asp Ala Ser Gly
         35                  40                  45

Thr Met Gly Gly Ala Cys Gly Tyr Gly Asn Leu Tyr Ser Gln Gly Tyr
     50                  55                  60

Gly Val Asn Thr Ala Ala Leu Ser Thr Ala Leu Phe Asn Asn Gly Leu
65                  70                  75                  80

Ser Cys Gly Ala Cys Phe Glu Leu Lys Cys Thr Asn Thr Pro Asn Trp
                 85                  90                  95

Lys Trp Cys Leu Pro Gly Asn Pro Ser Ile Leu Ile Thr Ala Thr Asn
            100                 105                 110

Phe Cys Pro Pro Asn Tyr Ala Leu Pro Asn Asp Asn Gly Gly Trp Cys
        115                 120                 125

Asn Pro Pro Arg Pro His Phe Asp Leu Ala Met Pro Met Phe Leu Lys
    130                 135                 140

Leu Ala Gln Tyr Arg Ala Gly Ile Val Pro Val Thr Tyr Arg Arg Ile
145                 150                 155                 160

Pro Cys Arg Lys Gln Gly Gly Ile Arg Phe Thr Ile Asn Gly Phe Arg
                165                 170                 175

Tyr Phe Asn Leu Val Leu Ile Thr Asn Val Ala Gly Ala Gly Asp Ile
            180                 185                 190

Ile Lys Val Trp Val Lys Gly Thr Lys Thr Asn Trp Ile Pro Leu Ser
        195                 200                 205

Arg Asn Trp Gly Gln Asn Trp Gln Ser Asn Ala Val Leu Thr Gly Gln
    210                 215                 220

Ser Leu Ser Phe Arg Val Lys Ala Ser Asp His Arg Ser Ser Thr Ser
225                 230                 235                 240

Trp Asn Met Val Pro Ser His Trp Gln Phe Gly Gln Thr Phe Ile Gly
                245                 250                 255

Lys Asn Phe Lys Ile
            260
```

TOMATOES THAT SOFTEN MORE SLOWLY POST-HARVEST DUE TO NON-TRANSGENIC ALTERATIONS IN AN EXPANSIN GENE

CROSS-REFERENCE TO RELATED APPLICATIONS

This application is a divisional of U.S. application Ser. No. 13/002,103, filed Dec. 30, 2010, which is a United States §371 National Phase application of PCT/US2009/049430, filed Jul. 1, 2009, both of which claim the benefit of U.S. Provisional Application No. 61/077,453, filed Jul. 1, 2008, all of which are hereby incorporated by reference in their entirety.

STATEMENT REGARDING FEDERALLY SPONSORED RESEARCH OR DEVELOPMENT

This invention was made with Government support under Contract No. W911QY-07-C-0121 awarded by the United States Department of Defense. The Government has certain rights in the invention.

FIELD OF THE INVENTION

This invention relates to human-induced non-transgenic mutations in an expansin gene of tomato, particularly, LeExp1, and tomato plants having such non-transgenic mutations in at least one of their expansin genes, more particularly, an LeExp1 gene. This invention further relates to tomato plants having delayed post-harvest softening of their fruits as a result of non-transgenic mutations in at least one of their LeExp1 genes. This invention further relates to a method of creating non-transgenic tomato plants exhibiting delayed post-harvest fruit softening. In addition, this invention concerns a novel partial genomic DNA sequence for LeExp1.

BACKGROUND

One of the main challenges facing the tomato industry is how to deliver to a processing plant or to the marketplace tomato fruit that have been vine-ripened (i.e., desirable to consumers in taste, texture, and color) but that remain firm without the usual softening that reduces the shelf life of harvested fruit. Because traditional breeding methods are very labor intensive, it could take years to develop a novel tomato variety that may display only a modest increase in shelf life. Recent studies have utilized genetic and biochemical techniques in an effort to identify the factors that affect fruit softening. By identifying and modifying the expression of specific genes that are involved in cell wall degradation, researchers and breeders hope to develop new tomato varieties that have the desirable qualities of vine-ripened fruit, but that also are resistant to post-harvest softening and, therefore, display a longer shelf life with reduced spoilage.

Fruit softening is one of the many ripening-related changes, including alterations in fruit texture, color, aroma, and metabolism of sugars and organic acids, which occur as a result of a developmental program triggered by ethylene. Recent data indicate that cell wall proteins called expansins are important regulators of fruit softening in tomato fruit. This large multigene family of proteins has been proposed to loosen cell walls and stimulate plant cell enlargement by weakening the non-covalent bonds between glucans. The observation that mRNA and protein for LeExp1, the primary expansin expressed in tomato fruit, is upregulated with ripening led to the hypothesis that this protein is involved in cell wall disassembly. Consistent with this idea, treatment of green wild type fruit with ethylene gas results in a rapid and robust rise in LeExp1 mRNA whereas LeExp1 expression levels are not increased by ethylene in ripening-impaired rin mutant tomatoes (Rose et al., *Proceedings of the National Academy of Sciences USA* 94:5955-5960, 1997).

Antisense expression of a LeExp1 transgene in tomato plants has confirmed the importance of the expansins to the commercial tomato industry. Fruit of tomato plants expressing an antisense LeExp1 transgene under the direction of a constitutively expressed promoter have reduced endogenous Exp1 levels and increased firmness compared to wild type tomato fruit. In contrast, expression of a sense LeExp1 transgene increased Exp1 mRNA and protein levels in tomato fruit and enhanced fruit softening (Brummell et al., *The Plant Cell* 11:2203-2216, 1999; U.S. Pat. No. 6,350,935). An antisense LeExp1 transgene also affects tomato processing qualities for juice and paste (Kalamaki et al., *Journal of Agricultural and Food Chemistry* 51(25):7465-7471, 2003; Kalamaki et al., *Journal of Agricultural and Food Chemistry* 51(25):7456-7464, 2003).

These data suggest that modulation of LeExp1 levels in tomatoes affects fruit softening, a key factor that limits the shelf life of fresh tomatoes. However, numerous expansins with overlapping patterns of expression are detectable in tomato fruit during development. This observation opens the possibility that the antisense LeExp1 transgene reduces not only LeExp1, but also suppresses the expression of other expansins. The method described herein specifically targets the LeExp1 gene and plants generated by this method contain mutations in LeExp1.

Transgenic technology has successfully utilized antisense LeExp1 transgenes to reduce post-harvest softening in tomato fruit. However, public acceptance of genetically modified plants, particularly with respect to plants used for food, is not universal. Alternatively, traditional breeding methods could be used to develop new tomato varieties with reduced expansin protein levels or activity. However, these methods are both laborious and time-consuming. In addition, undesirable characteristics often are transferred along with the desired traits when tomato plants are crossed in traditional breeding programs.

Because some consumers have clear preferences against genetically modified foods, it would be useful to have a tomato that exhibits reduced levels of LeExp1, but that is not the result of genetic engineering. However, to date, a naturally occurring "knockout" or "knockdown" of any endogenous tomato expansin gene is not known in the art. The inventors have screened an 802 base pair region of the LeExp1 gene in 183 commercial, heirloom and collected tomato varieties to assess existing natural genetic variation. The inventors uncovered one mutation in an intronic region of the LeExp1 gene, but no mutations in its coding region. These findings indicate the lack of natural genetic variation in the LeExp1 gene of germplasm that is available to tomato breeders. The availability of multiple allelic mutations in LeExp1 would provide tomato breeders with novel genetic variation and a spectrum of phenotypes for the development of new firmer fleshed tomato varieties. A cultivated tomato with reduced fruit softening as a result of its LeExp1 gene either knocked out or otherwise hindered that was not the result of genetic engineering would have tremendous value for the tomato industry, including fresh market tomatoes, processor tomatoes and tomato food products such as sliced tomatoes, canned tomatoes, ketchups, soups, sauces, juices and pastes.

SUMMARY OF THE INVENTION

In accordance with one exemplary embodiment, this invention includes a tomato plant, tomatoes, seeds, plant parts and progeny thereof exhibiting a decreased rate of post-harvest softening caused by a human induced non-transgenic mutation in at least one LeExp1 gene.

In accordance with another exemplary embodiment, this invention includes a tomato plant containing a mutated LeExp1 gene, as well as fruit, seeds, pollen, plant parts and progeny of that plant.

In accordance with yet another exemplary embodiment, this invention includes food and food products incorporating fruit from tomato plants exhibiting a decreased rate of post-harvest softening caused by a human-induced non-transgenic mutation in at least one LeExp1 gene.

In accordance with another exemplary embodiment, this invention includes a method of creating tomato plants with fruit exhibiting delayed post-harvest softening, comprising the steps of: obtaining plant material from a desired cultivar of tomato plant; inducing point mutations in at least one LeExp1 gene of the plant material by treating the plant material with a mutagen; growing the mutagenized plant material to produce tomato plants; isolating genomic DNA from the tomato plants or from progeny of the tomato plant; amplifying segments of an LeExp1 gene from the genomic DNA of the tomato plants or the progeny of the tomato plant using PCR primers specific to the LeExp1 gene or to the DNA sequences adjacent to the LeExp1 gene; and detecting point mutations in the LeExp1 gene of at least one tomato plant.

In accordance with another exemplary embodiment, this invention includes a tomato plant, fruit, seeds, pollen or plant parts created according to the method described herein.

BRIEF DESCRIPTION OF THE SEQUENCE LISTING

SEQ ID NO: 1 shows *Lycopersicon esculentum* expansin (LeExp1) mRNA, complete cds. (GenBank Accession Number U82123).

SEQ ID NOs: 2-5 show the DNA sequences for *Lycopersicon esculentum* expansin (LeExp1) specific primers of the present invention used for genomic sequencing.

SEQ ID NO: 6 shows the DNA sequence of a PCR product that comprises a genomic DNA sequence for *Lycopersicon esculentum* expansin (LeExp1).

SEQ ID NOs: 7-10 show the DNA sequences for *Lycopersicon esculentum* expansin (LeExp1) specific primers of the present invention used for mutation detection.

SEQ ID NO: 11 shows the protein encoded by SEQ ID NO: 1 (GenBank Accession Number AAC63088).

DETAILED DESCRIPTION OF PREFERRED EMBODIMENTS

The present invention describes tomato plants exhibiting delayed post-harvest softening of their tomato fruits without the inclusion of foreign nucleic acids in the tomato plants' genomes. The present invention further describes a series of independent non-transgenic mutations in an LeExp1 gene of tomato; a tomato plant having one or more of these mutations in the LeExp1 gene thereof; and a method of creating and identifying similar and/or additional mutations in at least one LeExp1 gene of a tomato plant. Further, the present invention describes a novel partial genomic DNA sequence for LeExp1, as well as the use of this sequence and functional equivalents thereof to modify post-harvest softening in tomato fruit.

In order to create and identify the LeExp1 gene mutations and tomatoes of the present invention, a method known as TILLING® was utilized. See McCallum et al., *Nature Biotechnology* 18:455-457, 2000; McCallum et al., *Plant Physiology* 123:439-442, 2000; U.S. Pat. No. 5,994,075; and U.S. Publication No. 20040053236, all of which are incorporated herein by reference. In the basic TILLING® methodology, plant material, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of tomato having at least one expansin gene with substantial percent identity to SEQ ID NO: 6 may be used in the present invention. As used herein, "substantial percent identity" means that the DNA sequence of the gene is sufficiently similar to SEQ ID NO: 6 at the nucleotide level to code for the same protein as SEQ ID NO: 6, allowing for allelic differences between tomato cultivars. In accordance with one aspect of an exemplary embodiment of the invention, "substantial percent identity" may be present when the percent identity in the coding region between the expansin gene and SEQ ID NO: 6 is as low as about 85%, provided that percent identity in the conserved regions of the coding region of the gene is higher (e.g., at least about 90%). Preferably, the percent identity in the coding region is about 85-90%, more preferably about 90-95%, and optimally, greater than about 95%. One of skill in the art may prefer a tomato cultivar having commercial popularity or one having specific desired characteristics in which to create the LeExp1-mutated tomato plants. Alternatively, one of skill in the art may prefer a tomato cultivar having few polymorphisms, such as an in-bred cultivar, in order to facilitate screening for mutations within an LeExp1 gene.

In accordance with one aspect of an exemplary embodiment of the present invention, seeds from a tomato plant were mutagenized and then grown into M1 plants. The M1 plants were then allowed to self-pollinate and seeds from the M1 plant were grown into M2 plants, which were then screened for mutations in their LeExp1 genes. M1 plants can be screened for mutations but an advantage of screening the M2 plants is that all somatic mutations correspond to the germline mutations. One of skill in the art would understand that a variety of tomato plant materials, including, but not limited to, seeds, pollen, plant tissue or plant cells, may be mutagenized in order to create an LeExp1-mutated tomato plant of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for LeExp1 gene mutations instead of waiting until the M2 generation.

Mutagens that create primarily point mutations and short deletions, insertions, transversions, and/or transitions (about 1 to about 5 nucleotides), such as chemical mutagens or radiation, may be used to create the mutations of the present invention. Mutagens conforming with the method of the present invention include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloro-ethyl)aminopropylamino] acridine dihydrochloride (ICR-170), and formaldehyde. Spontaneous mutations in an LeExp1 gene that may not have been directly caused by the mutagen can also be identified using the present invention.

Any suitable method of plant DNA preparation now known or hereafter devised may be used to prepare the tomato plant DNA for LeExp1 mutation screening. For example, see Chen and Ronald, *Plant Molecular Biology Reporter* 17: 53-57, 1999; Stewart and Via, *Bio Techniques* 14:748-749, 1993. Additionally, several commercial kits are available, including kits from Qiagen (Valencia, Calif.) and Qbiogene (Carlsbad, Calif.).

In accordance with one aspect of an exemplary embodiment of the invention, prepared DNA from individual tomato plants is pooled in order to expedite screening for mutations in the LeExp1 genes of the entire population of plants originating from the mutagenized plant tissue. The size of the pooled group may be dependent upon the sensitivity of the screening method used. Preferably, groups of four or more individual tomato plants are pooled.

In accordance with another aspect of an exemplary embodiment, after the DNA samples are pooled, the pools are subjected to LeExp1 gene-specific amplification techniques, such as Polymerase Chain Reaction (PCR). For a general overview of PCR, see PCR Protocols: A Guide to Methods and Applications (Inns, Gelfand, Sninsky, and White, eds.), Academic Press, San Diego, 1990. Any primer specific to an LeExp1 gene or the sequences immediately adjacent to an LeExp1 gene may be utilized to amplify an LeExp1 gene within the pooled DNA sample. Preferably, the primer is designed to amplify the regions of the LeExp1 gene where useful mutations are most likely to arise. Most preferably, the primer is designed to detect mutations in the coding region of the LeExp1 gene. Additionally, it is preferable for the primer to avoid known polymorphic sites in order to ease screening for point mutations. To facilitate detection of PCR products on a gel, the PCR primer may be labeled using any conventional or hereafter devised labeling method.

In accordance with one exemplary embodiment of the present invention, a partial genomic DNA sequence for the LeExp1 gene was constructed. Based upon the previously published LeExp1 complete cds. sequence GenBank Accession Number U82123 (SEQ ID NO: 1), sets of primers were designed that amplified overlapping segments of tomato genomic DNA. PCR products were sequenced and a continuous DNA sequence was deduced by aligning these overlapping segments.

Exemplary primers (SEQ ID NOs: 2-5) that proved useful for identifying a partial genomic DNA sequence for LeExp1 are shown below in Table 1.

TABLE 1

Exemplary Genomic Sequencing Primers

| SEQ ID | Primer Name | Primer ID | Sequence |
|---|---|---|---|
| 2 | LeExp3-L | PR-1333 | CCTGGAAACCCTTCCATTTTAATCACAG |
| 3 | LeExp1-R | PR-1334 | CATGATTTTGCAGCCACTTCAACCTTTC |

TABLE 1-continued

Exemplary Genomic Sequencing Primers

| SEQ ID | Primer Name | Primer ID | Sequence |
|---|---|---|---|
| 4 | LeExp-2L | PR-3312 | TACATTTTACGGCGGAAGTGATGCTTCT |
| 5 | LeExp-3R | PR-3313 | TGATTGACCAGTTAAAACCGCATTTGAT |

Exemplary primers (SEQ ID NOs: 7-10) that proved useful for identifying mutations in LeExp1 are shown below in Table 2. The primers S1Exp-AL and S1Exp-AR made up primer pair A and S1Exp-BL and S1Exp-BR made up primer pair B.

TABLE 2

Exemplary Primers Useful for Mutation Detection

| SEQ ID | Primer Name | Primer ID | Sequence |
|---|---|---|---|
| 7 | S1Exp-BL | PR-2878 | TCAATTCCATTAAATCTTAAGAATGGGTATCA |
| 8 | S1Exp-BR | PR-2879 | TTTCCAAAAGTTAGCTCAAACGGAGGAAGATT |
| 9 | S1Exp-AL | PR-2790 | CCTGGAAACCCTTCCATTTTAATCACAG |
| 10 | S1Exp-AR | PR-2791 | CATGATTTTGCAGCCACTTCAACCTTTC |

In accordance with one aspect of an exemplary embodiment of the invention, the PCR amplification products may be screened for LeExp1 mutations using any method that identifies nucleotide differences between wild type and mutant genes. These may include, without limitation, sequencing, denaturing high pressure liquid chromatography (dHPLC), constant denaturant capillary electrophoresis (CDCE), temperature gradient capillary electrophoresis (TGCE) (see Li et al., *Electrophoresis* 23(10):1499-1511, 2002), or by fragmentation using enzymatic cleavage, such as used in the high throughput method described by Colbert et al., *Plant Physiology* 126:480-484, 2001. Preferably, the PCR amplification products are incubated with an endonuclease that preferentially cleaves mismatches in heteroduplexes between wild type and mutant. In accordance with another aspect of an exemplary embodiment, cleavage products are electrophoresed using an automated sequencing gel apparatus, and gel images are analyzed with the aid of a standard commercial image-processing program.

The present inventors have determined that to achieve reduced post-harvest softening in tomatoes, mutations that reduce LeExp1 function in tomato fruit are desirable. Preferred mutations include missense, nonsense and splice junction changes, including mutations that prematurely truncate the translation of the LeExp1 protein from messenger RNA, such as those mutations that create a stop codon within the coding regions of the LeExp1 gene. Such mutations include point mutations, insertions, repeat sequences, and modified open reading frames (ORFs).

In accordance with yet another aspect of an exemplary embodiment of the invention, once an M2 plant having a mutated LeExp1 gene is identified, the mutations are analyzed to determine its affect on the expression, translation, and/or protein level of LeExp1. In accordance with one exemplary embodiment, the PCR fragment containing the mutation is sequenced, using standard sequencing techniques, in order to determine the exact location of the mutation within the LeExp1 gene sequence. Each mutation is evaluated in order to predict its impact on protein function (i.e., completely tolerated to loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function.

In accordance with a further aspect of an exemplary embodiment, if the initial assessment of a mutation in an M2 plant indicates it to be of a useful nature and in a useful position within an LeExp1 gene, then further phenotypic analysis of the tomato plant containing that mutation is pursued. First, the M2 plant is backcrossed or outcrossed twice to create a BC1 plant in order to eliminate background mutations. Then, the backcrossed or outcrossed BC1 plant is self-pollinated in order to create a BC1F2 plant that is homozygous for the LeExp1 mutation.

Physical characteristics of the homozygous LeExp1 mutant plants are then assessed by physical observation over a period of time. Mutant LeExp1 tomatoes are evaluated for delays in post-harvest softening compared to tomatoes derived from the normal (e.g., wild type) parental tomato lines or to wild type (for LeExp1) sibling controls. Tomato fruit ripening is often evaluated by at least the following characteristics: color, texture, slice integrity, percentage of solids, and acidity (see, e.g., Cantwell, M., Report to the California Tomato Commission: Tomato Variety Trials: Postharvest Evaluations for 2001; Edan et al., *Journal of Food Science* 62(4): 793-796, 1997; Errington et al., *Postharvest Biology and Technology* 11:141-147, 1997; Lesage and Destain, *Postharvest Biology and Technology* 8:45-55, 1996; Malundo et al., *Postharvest Biology and Technology* 6:103-110, 1995; and McGuire, *HortScience* 27(12): 1254-1255, 1992.)

Normal tomato fruit ripens such that the color of the tomato changes from light green to red. These changes can be measured reflectively at various wavelengths of light. As this change happens, the fruit tends to become softer such that compression distance under a specified weight increases and/or the force required to depress the surface of the fruit a specified distance decreases. Along with softening, the ratio of liquid/juice within the tomato to solids as the fruit ripens. Slice integrity, expressed as a percentage of juice weight by total weight of the slice, is a measure of the amount of free juice that drains from a freshly cut slice of tomato (of specified thickness). The degree of soluble solids is measured by pureeing the tomato using a specified protocol and filtering the tomato pulp from its juice. The refractive index of the juice is then taken as a measure of soluble solids. The degree of acidity in the juice is measured by titration of a specified volume of juice with sodium hydroxide to a neutral pH and is expressed as a percentage of the total weight of the juice.

The present inventors have observed that tomatoes carrying mutations in at least one of their LeExp1 genes remain firm longer than wild type tomatoes from their parental lines or wild type sibling controls. Alternative measures of ripeness, such as hyper spectral image analysis for a detailed measure of the color of the ripening tomatoes or sampling of the volatile organics emitted by the ripening tomatoes may yield further information and more discriminate information on the exact degree of ripeness in the LeExp1 mutant tomatoes (see, e.g., Polder et al., Hyperspectral Image Analysis for Measuring Ripeness of Tomatoes, 2000 American Society of Agricultural Engineers International Meeting, Milwaukee, Wis., July 2000; Butrym and Hartman, An Apparatus for Sampling Volatile Organics from Live Plant Material Using Short Path Thermal Desorption, Eastern Analytical Symposium, Somerset, N.J., November 1998). These assays, combined with the standard measures, may also allow measurement of enhancements in the flavor of the LeExp1 mutant tomatoes at a given stage of tomato softness.

The following mutations identified in Table 4 are exemplary of the mutations created and identified according to various embodiments of the present invention. They are offered by way of illustration only, and not limitation. It is to be understood that the mutations below are merely exemplary and that similar mutations are also contemplated.

TABLE 4

Examples of mutations created and identified in LeExp1 in tomato. Nucleotide and amino acid changes are identified according to SEQ ID NOs: 6 and 11, respectively.

| Original Variety | Gene | Primer Pair | DNA Change | Protein Change | Type of Mutation |
|---|---|---|---|---|---|
| NC | Exp | EXP-B | G220T | G65* Gly65Stop | STOP |
| NC | Exp | EXP-B | G274A | G83R Gly83Arg | Severe missense |
| NC | Exp | EXP-B | C305T | T93I Thr93Ile | Severe missense |
| NC | Exp | EXP-B | G403A | G126S Gly126Ser | Severe missense |
| NC | Exp | EXP-B | C460T | L145F Leu145Phe | Severe missense |
| SL | Exp | EXP-A | G937A | G190R Gly190Arg | Severe missense |
| NC | Exp | EXP-A | G940T | D191Y Asp191Tyr | Severe missense |
| SL | Exp | EXP-A | C986T | P206L Pro206Leu | Missense |
| NC | Exp | EXP-A | A991G | S208G Ser208Gly | Missense |
| SL | Exp | EXP-A | G1001A | W211* Trp208Stop | STOP |

EXAMPLE 1

Mutagenesis

Tomato seeds of cultivars Shady Lady (hybrid) and NC 84173 (an inbred line provided by R. Gardner at UNC) were vacuum infiltrated in $H_2O$ (approximately 1000 seeds/100 ml $H_2O$ for approximately 4 minutes). The seeds were then placed on a shaker (45 rpm) in a fume hood at ambient temperature. The mutagen ethyl methanesulfonate (EMS) was added to the imbibing seeds to final concentrations ranging from about 0.1% to about 1.6% (v/v). EMS concentrations of about 0.4 to about 1.2% are preferable in accordance with one aspect of an exemplary embodiment of the invention. Following a 24-hour incubation period, the EMS solution was replaced 4 times with fresh $H_2O$. The seeds were then rinsed under running water for ca. 1 hour. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from the M2 plants produced in accordance with the above description was extracted and prepared in order to identify which M2 plants carried a mutation at their LeExp1 loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5600×g. Next, 800 µl of Buffer AW was added to each well of the filter plate, sealed and spun for 15 minutes at 5600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

TILLING®

The M2 DNA was pooled into groups of four individuals each. For pools containing four individuals, the DNA concentration for each individual within the pool was 0.25 ng/µl with a final concentration of 1 ng/µl for the entire pool. The pooled DNA samples were arrayed on microtiter plates and subjected to gene-specific PCR.

PCR amplification was performed in 15 µl volumes containing 5 ng pooled or individual DNA, 0.75× ExTaq buffer (Panvera®, Madison, Wis.), 2.6 mM $MgCl_2$, 0.3 mM dNTPs, 0.3 µM primers, and 0.05U Ex-Taq (Panvera®) DNA polymerase. PCR amplification was performed using an MJ Research® thermal cycler as follows: 95° C. for 2 minutes; 8 cycles of "touchdown PCR" (94° C. for 20 seconds, followed by an annealing step starting at 70-68° C. for 30 seconds decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds –0.3 degrees/cycle.

The PCR primers (MWG Biotech, Inc., High Point, N.C.) were mixed as follows:

9 µl 100 µM IRD-700 labeled left primer
1 µl 100 µM left primer
10 µl 100 µM right primer The IRD-700 label can be attached to either the right or left primer. Preferably, the labeled to unlabeled primer ratio is 9:1. Alternatively, Cy5.5 modified primers or IRD-800 modified primers could be used. The label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, and CEL 1 (Transgenomic®, Inc.; 1:100,000 dilution) was added with mixing on ice, and the plate was incubated at 45° C. for 15 minutes. The specific activity of the CEL1 was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at 80° C., spun at 4000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 hours at 1,500-V, 40-W, and 40-mA limits at 50° C.

During electrophoresis, the gel was imaged using a LI-COR® (Lincoln, Nebr.) scanner which was set at a channel capable of detecting the IR Dye 700 label. The gel image showed sequence-specific pattern of background bands common to all 96 lanes. Rare events, such as mutations, create new bands that stand out above the background pattern. Plants with bands indicative of mutations of interest were evaluated by TILLING® individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation).

Physical and Biochemical Measurements

Tomatoes Selected for Study:

Individual tomatoes selected for study were picked from plants derived from siblings of the same cross to preserve background phenotypes as much as possible. In some cases, mutants were backcrossed to tomato line NC 84173, and in other cases mutants were backcrossed to tomato line FLA 8059. Using two independent tomato lines elucidates possible background specific effects on phenotype. The plants and fruit were genotyped as homozygous for the mutation, heterozygous for the mutation, or wild type. Genotyping was performed using Taqman SNP Genotyping Assays (Applied Biosystems) to discriminate the three different alleles of the LeExp1 locus.

Measurement of Fruit Firmness:

Fruit (homozygous and wild-type siblings) were harvested at breaker stage and allowed to ripen at room temperature to light red stage. After the light red stage, tomatoes were stored at 55° F. Firmness was measured using a model TA-XT Texture Analyzer (Texture Technologies, Scarsdale, N.Y.). The amount of force required to depress the tomato fruit surface 5 mm was recorded for each sample. Fruit firmness was measured twice for each fruit, equatorially, at two time points. The first two measurement locations were marked on the fruit, and subsequent measurements were taken at least 7 days later at different equatorial locations. Thus, each fruit was depressed four times. In general, time points were 7 days or increments of 7 days apart.

Measurement of Rot Rate:

A minimum of 10 fruit for each genotype were harvested at the breaker stage of fruit development and ripened to red prior to commencing the study to ensure that tomatoes of each type were at the same physiological age. Tomatoes were stored at 55° F. and evaluated on a weekly basis for signs of rot. The rot rate was then calculated over time as the percent of tomatoes exhibiting rot. In all cases, homozygote fruit were compared to wild type sibling controls.

Measurement of Field Holding:

Field holding is measured by delaying fruit harvest from the field for several weeks beyond the optimal harvest window and then counting the number of intact fruit left in equivalent sized plots for each test group.

Identification and Evaluation of Mutation G220T

DNA from a tomato plant originating from seeds of cultivar NC84173 that were incubated in 1.2% EMS, was amplified using primer pair EXP-B (TILLING primers S1Exp-BL and S1Exp-BR, SEQ ID NOs: 7 and 8). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in an LeExp1 gene. Sequence analysis of this fragment showed the mutation was a guanine to thymine change at nucleotide 220 of SEQ ID NO: 6. This mutation correlates with a change from glycine at amino acid 65 of the LeExp1 protein shown in SEQ ID NO: 11 to a stop mutation.

Fruit from plants homozygous for the G220T mutation were more than 20 percent firmer than fruit from wild type sibling plants, and this phenotype was repeated in a subsequent generation, verifying its heritability. Homozygous fruit also withstood the onset of rot for an average of 7 days beyond the onset of rot seen in wild type plants. In addition, homozygous fruit demonstrated superior field holding compared to wild type sibling controls. Compositional analysis of organic acids, pH and Brix showed no differences between homozygous and wild type controls, confirming that the LeExp1 mutation did not alter fundamental tomato qualities.

Identification and Evaluation of Mutation G1001A

DNA from a tomato plant originating from seeds of cultivar Shady Lady that were incubated in 1.2% EMS, was amplified using primer pair EXP-A (TILLING primers S1Exp-AL and S1Exp-AR, SEQ ID NOs: 9 and 10). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in an LeExp1 gene. Sequence analysis of this fragment showed the mutation was a guanine to adenine change at nucleotide 1001 of SEQ ID NO: 6. This mutation correlates with a change from tryptophan at amino acid 211 of the LeExp1 protein shown in SEQ ID NO: 11 to a stop mutation.

Fruit from plants homozygous for the G1001A mutation were more than 20 percent firmer than fruit from wild type siblings.

Identification and Evaluation of Mutation G274A

DNA from a tomato plant originating from seeds of cultivar NC84173 that were incubated in 1.2% EMS, was amplified using primer pair EXP-B (TILLING primers S1Exp-BL and S1Exp-BR, SEQ ID NOs: 7 and 8). The PCR amplification products were then incubated with CEL 1 and electrophoresed. The electrophoresis gel image showed a fragment which stood out above the background pattern for the PCR amplification products. Therefore, it was likely that this fragment contained a heteroduplex created by a mutation in an LeExp1 gene. Sequence analysis of this fragment showed the mutation was a guanine to adenine change at nucleotide 274 of SEQ ID NO: 6. This mutation correlates with a change from glycine at amino acid 83 of the LeExp1 protein shown in SEQ ID NO: 11 to arginine.

Fruit from plants homozygous for the G274A mutation were more than 20 percent firmer than fruit from wild type sibling plants after 21 days post-harvest.

The above examples are provided to illustrate the invention but not limit its scope. Other variants of the invention will be readily apparent to one of ordinary skill in the art and are encompassed by the appended claims and all their equivalents. All publications, patents, and patent applications cited herein are hereby incorporated by reference.

We claim:

1. A method of producing a tomato plant comprising the steps of:
    (a) screening DNA from at least one tomato plant for mutations in an LeExp1 gene;
    (b) selecting for a tomato plant having a mutation in said LeExp1 gene, wherein said mutation is a nucleotide change selected from the group consisting of G220T, G274A, and G1001A and wherein said nucleotide change is identified through the comparison to SEQ ID NO: 6; and
    (c) further selecting for a tomato plant having said mutation that, when homozygous for said mutation and grown in the field, is capable of producing fruit that is firmer than wild type fruit not having said mutation.

2. The method of claim 1, wherein said mutation is a human-induced, non-transgenic mutation.

3. The method of claim 1, wherein said nucleotide change comprises G220T.

4. The method of claim 1, wherein said nucleotide change comprises G274A.

5. The method of claim 1, wherein said nucleotide change comprises G1001A.

6. A fruit, a seed, a pollen grain, a plant part or a progeny of a tomato plant identified by the method of claim 1, wherein the fruit, the seed, the pollen grain, the plant part, or the progeny comprises said mutation.

7. A food or a food product incorporating the fruit of claim 6.

8. A method of producing a tomato plant comprising the steps of:
(a) screening DNA from at least one tomato plant for mutations in an LeExp1 gene;
(b) selecting for a tomato plant having a mutation in said gene, wherein said mutation creates an amino acid change in the protein expressed from said gene, wherein said amino acid change is selected from G65*, G83R, and W211* and wherein said amino acid change is identified according to SEQ ID NO: 11; and
(c) further selecting for a tomato plant having said mutation that, when homozygous for said mutation and grown in the field, is capable of producing fruit that is firmer than wild type fruit not having said mutation.

9. The method of claim 8, wherein said mutation is a human-induced, non-transgenic mutation.

10. The method of claim 8, wherein said amino acid change comprises G65*.

11. The method of claim 8, wherein said amino acid change comprises G83R.

12. The method of claim 8, wherein said amino acid change comprises W211*.

13. A fruit, a seed, a pollen gain, a plant part or a progeny of a tomato plant identified by the method of claim 8, wherein the fruit, the seed, the pollen grain, the plant part, or the progeny comprises said mutation.

14. A food or a food product incorporating the fruit of claim 13.

* * * * *